(12) United States Patent
Jackson

(10) Patent No.: US 6,454,772 B1
(45) Date of Patent: Sep. 24, 2002

(54) SET SCREW FOR MEDICAL IMPLANT WITH GRIPPING SIDE SLOTS

(76) Inventor: Roger P. Jackson, 6600 Indian La., Mission Hills, KS (US) 66208

( * ) Notice: Subject to any disclaimer, the term of this patent is extended or adjusted under 35 U.S.C. 154(b) by 140 days.

(21) Appl. No.: 09/732,528

(22) Filed: Dec. 7, 2000

(51) Int. Cl.[7] ............................................ A61B 17/56
(52) U.S. Cl. ........................................ 606/73; 606/61
(58) Field of Search .............................. 606/73, 72, 76, 606/70, 61, 65, 69; 411/402, 403, 410, 393

(56) References Cited

U.S. PATENT DOCUMENTS

| | | |
|---|---|---|
| 791,548 A | 6/1905 | Fischer |
| 1,269,971 A * | 6/1918 | Smith ........................ 411/393 |
| 2,201,087 A | 5/1940 | Hallowell |
| 2,239,352 A | 4/1941 | Cherry |
| 2,295,314 A | 9/1942 | Whitney |
| 2,532,815 A | 12/1950 | Kindsvatter |
| 2,553,337 A | 5/1951 | Shafer |
| 2,778,265 A | 1/1957 | Brown |
| 2,877,681 A | 3/1959 | Brown |
| 2,927,332 A | 3/1960 | Moore |
| 3,143,029 A | 8/1964 | Brown |
| D200,217 S | 2/1965 | Curtiss |
| 3,370,341 A | 2/1968 | Allsop |
| 3,498,174 A | 3/1970 | Schuster et al. |

(List continued on next page.)

FOREIGN PATENT DOCUMENTS

| | | |
|---|---|---|
| DE | 3630863 | 3/1988 |
| DE | 373809 | 5/1989 |
| EP | 195455 | 9/1986 |
| EP | 172130 | 2/1987 |
| EP | 276153 | 7/1988 |
| EP | 465158 | 1/1992 |
| FR | 2467312 | 4/1981 |
| GB | 203508 | 9/1923 |
| WO | PCT92/03100 | 3/1992 |
| WO | PCT94/10927 | 5/1994 |
| WO | PCT9410944 | 5/1994 |
| WO | PCT96/06576 | 3/1996 |

* cited by examiner

Primary Examiner—Pedro Philogene
(74) Attorney, Agent, or Firm—John C. McMahon

(57) ABSTRACT

A set screw for locking a first implant in position relative to a second implant. The set screw having a bore with at least one side slot extending parallel to the axis of the screw and intersecting with an underside of the screw to produce an edge at such intersection. Preferably the slots also intersect with an upper surface of the bore to provide purchase for removal or insertion.

19 Claims, 5 Drawing Sheets

U.S. PATENT DOCUMENTS

| | | |
|---|---|---|
| 3,584,667 A | 6/1971 | Reiland |
| 3,812,757 A | 5/1974 | Reiland |
| 3,963,322 A | 6/1976 | Cryctko |
| 4,269,246 A | 5/1981 | Larson et al. |
| 4,492,500 A | 1/1985 | Ewing |
| 4,506,917 A | 3/1985 | Hansen Arne |
| 4,641,636 A | 2/1987 | Cotrel |
| 4,763,644 A | 8/1988 | Webb |
| 4,764,068 A | 8/1988 | Crispell |
| 4,790,297 A | 12/1988 | Luque |
| 4,815,453 A | 3/1989 | Cotrel |
| 4,838,264 A | 6/1989 | Bremer et al. |
| 5,005,562 A | 4/1991 | Cotrel |
| 5,067,955 A | 11/1991 | Cotrel |
| 5,073,074 A | 12/1991 | Corrigan et al. |
| 5,154,719 A | 10/1992 | Cotrel |
| 5,261,907 A | 11/1993 | Vignaud et al. |
| 5,261,912 A | 11/1993 | Frigg |
| 5,282,707 A | 2/1994 | Palm |
| 5,312,404 A | 5/1994 | Asher et al. |
| 5,346,493 A | 9/1994 | Stahurski et al. |
| 5,364,400 A | 11/1994 | Rego, Jr. et al. |
| 5,382,248 A | 1/1995 | Jacobson et al. |
| 5,385,583 A | 1/1995 | Cotrel |
| 5,487,742 A | 1/1996 | Cotrel |
| 5,496,321 A | 3/1996 | Puno et al. |
| 5,499,892 A | 3/1996 | Reed |
| 5,507,747 A | 4/1996 | Yuan et al. |
| 5,562,663 A | 10/1996 | Wisnewski et al. |
| 5,630,817 A | 5/1997 | Rokegem et al. |
| 5,643,260 A | 7/1997 | Doherty |
| 5,653,710 A | 8/1997 | Harle |
| 5,697,929 A * | 12/1997 | Mellinger ............... 411/5 |
| 6,059,786 A * | 5/2000 | Jackson ................ 606/61 |
| 6,102,913 A * | 8/2000 | Jackson ................ 411/5 |
| 6,220,805 B1 * | 4/2001 | Chang ................ 411/393 |

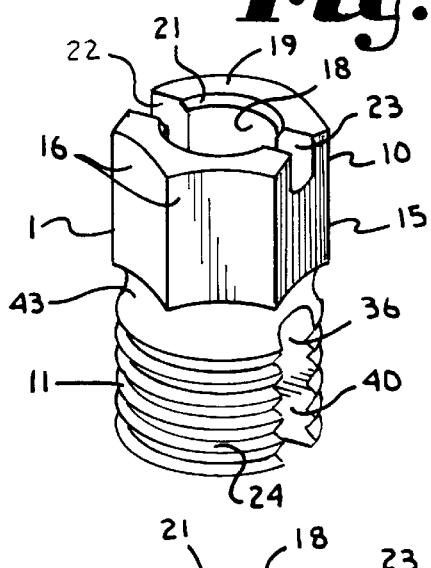
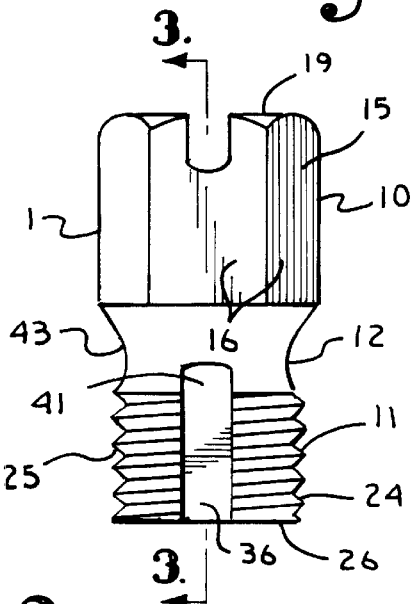
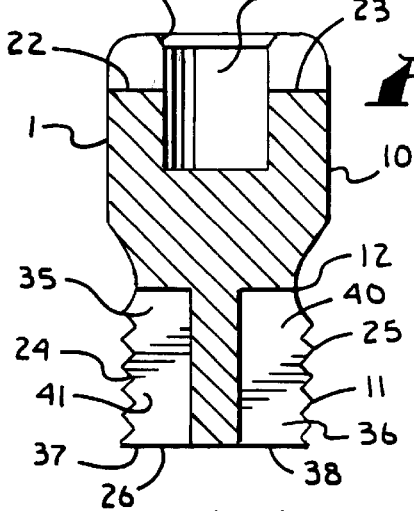
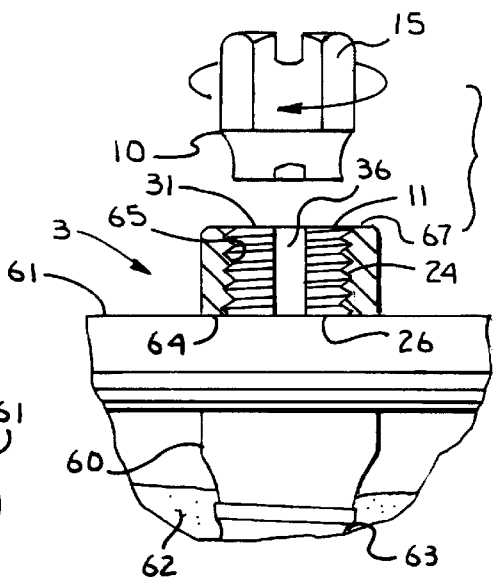
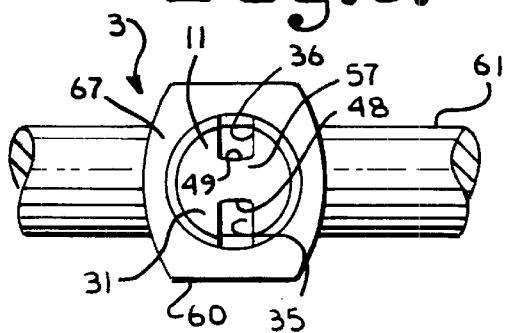

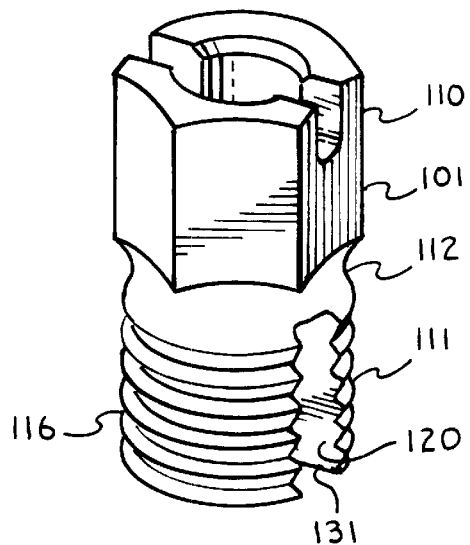
Fig.10.
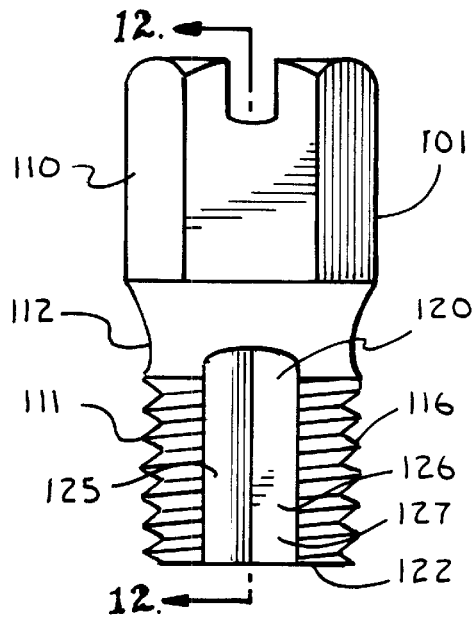
Fig.11.
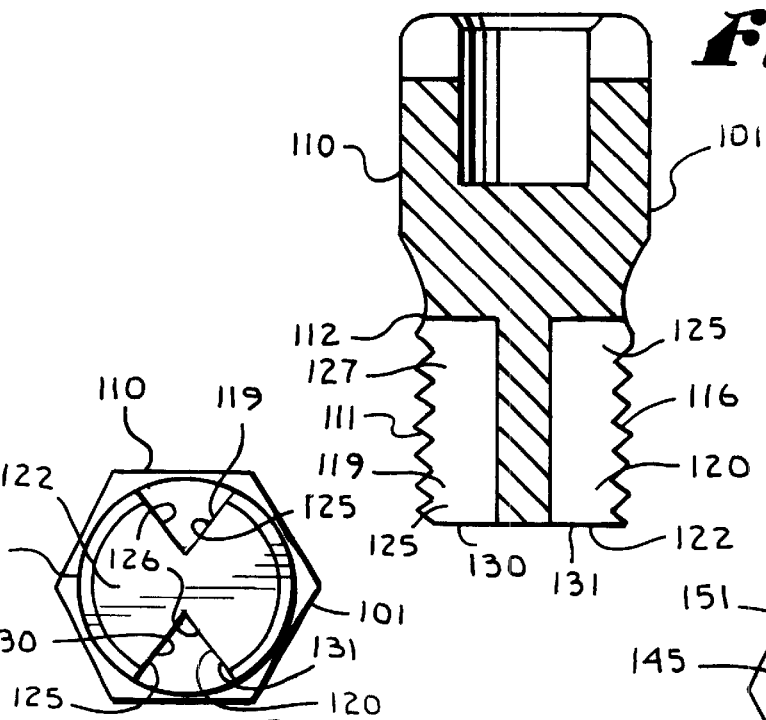
Fig.12.
Fig.13.
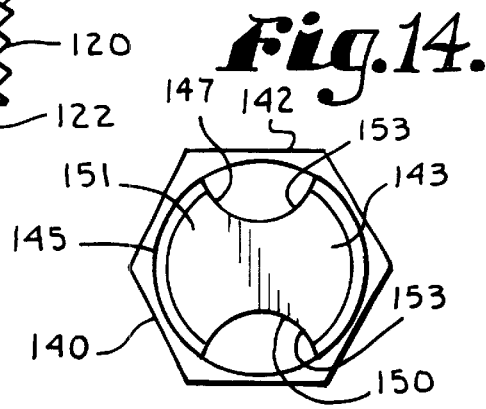
Fig.14.

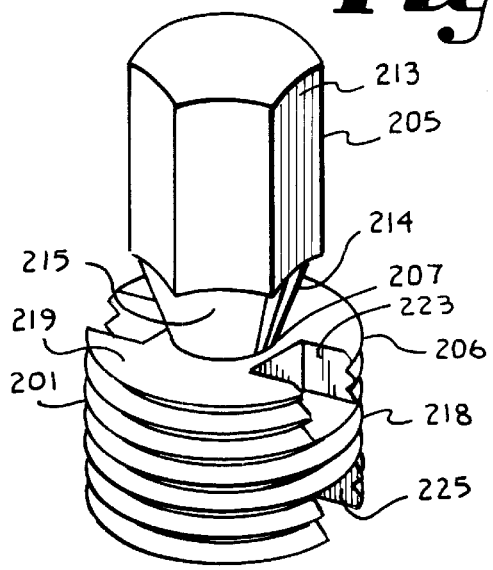
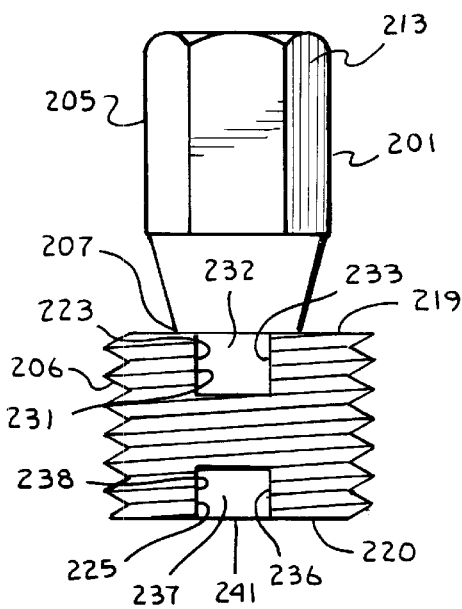
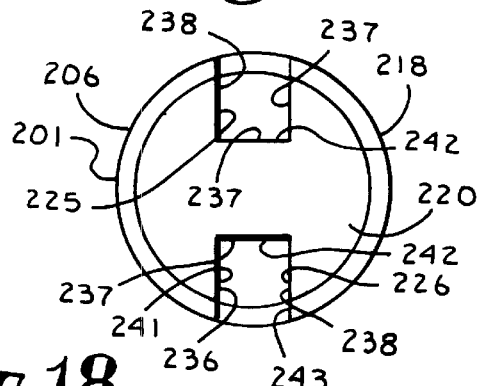

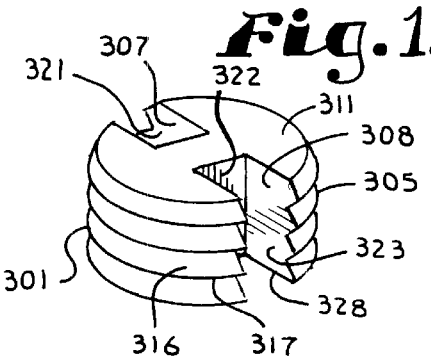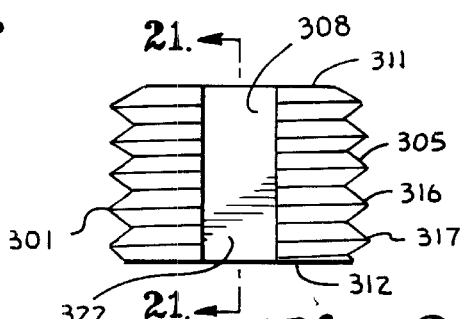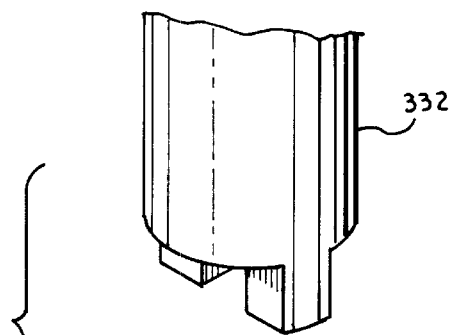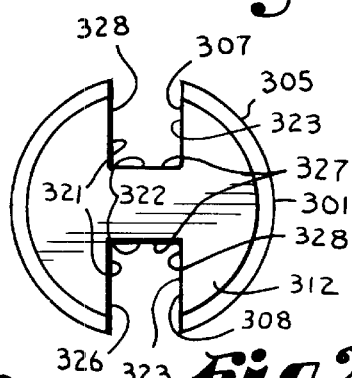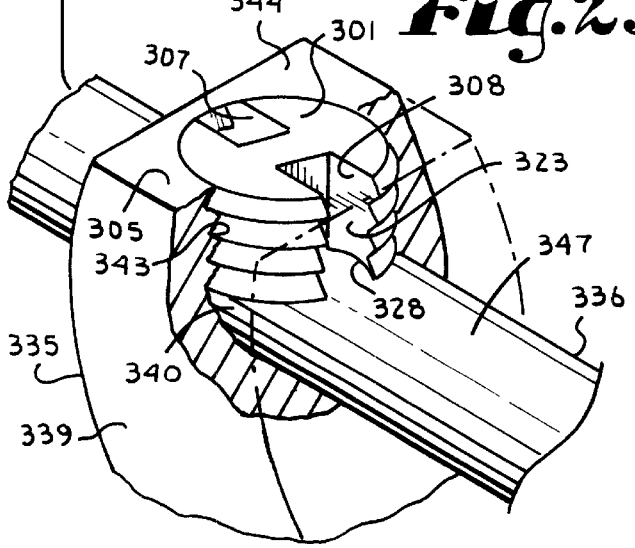

SET SCREW FOR MEDICAL IMPLANT WITH GRIPPING SIDE SLOTS

BACKGROUND OF THE INVENTION

The present application is directed to a set screw for use in applications where it is important for the set screw to have a clean and low profile after insertion, but for the set screw to grip the object against which the set screw sets and be removable, especially set screws for use in conjunction with medical implants.

Over recent years, medical implants for support of and correction of defects in various portions of the body, especially the spine, have improved dramatically. It is desirable to continue to improve these implants, so that the implants provide greater strength and durability and so that the implants are effective for the life of the patient. Furthermore, it is very desirable to provide such an implant which has low profile and interferes as little as possible with the living tissue surrounding the implant. In the past the set screw that secures together various parts of the implant, especially spinal implants, has often been a limiting factor with respect to such implants, the present invention is directed to improving such set screws.

Set screw manufacturers, especially for devices such as medical implants, are continually faced with the challenge of providing a set screw with the often conflicting goals of being small, lightweight, low profile and unobtrusive, while also being relatively quite strong and durable. Furthermore, it is desirable that the set screw be able to lock together two elements which very commonly include a rod positioned in a second medical implant. If the elements, such as rods, move axially or rotationally with respect to the other implants, the entire implant system may fail and may cause additional injury to the person within whom the implant is installed. Set screws used in spinal implants is are mainly of a first type that are screwed into a closed and threaded bore or a second type that are screwed between threaded surfaces of a pair of upstanding spaced arms in an implant which are often referred to as a plug.

Set screws used in medical implants are typically seven to ten millimeters in diameter. However, it is desirable to have yet smaller screws. One method of reducing the size of the screw without decreasing the strength is to decrease the outer diameter of the thread with or without changing the inner diameter of the thread by, in general, having the thread depth decrease. The overall strength of the implant is generally related to the inner diameter of the thread. Consequently, comparatively increasing the inner diameter or maintaining the inner diameter at the same diameter while decreasing the outer diameter can be effectively used to strengthen the set screw for a specific outer diameter.

When the inner diameter of the thread is increased or the outer diameter of the thread is decreased and the inner diameter remains the same, the pitch of the thread, which is the width between two peaks of the thread and which is sometimes measured in the number of threads per inch, is increased. That is, the thread becomes finer and, the depth of the thread becomes less and the distance between the peaks of adjacent turns of the thread becomes decreased. While increasing the thread inner diameter does increase the strength of the set screw, there is a point of diminishing returns whereat the thread depth is too little to grip between opposed threads and there is slippage. It has been found through experimentation that the thread depth which gives the greatest strength and yet does not slip may vary somewhat with size. Thus it has been found that in a 6 mm. diameter set screw, a pitch ratio of 0.4 may allow slippage whereas a pitch ratio of 0.5 to 0.55 provides substantial strength and resists slippage.

Not only does the finer thread aid in increasing the strength of the set screw, it is also better facilitates threads of opposed threaded elements aligning with one another. In particular, as mentioned above, some of the set screws in accordance with the present invention are used with implants having spaced arms having threaded interior surfaces. In such implants the set screw engages two discontinuous threaded surfaces. This can lead to inadvertent cross-threading where one turn of the thread of the set screw is lined up with two different turns of the thread on the facing surfaces of the arms. The finer thread, as discussed above, reduces the likelihood that a surgeon will inadvertently initiate cross-threading when the surgeon begins to install the set screw into a threaded receptacle for the screw.

As mentioned above, it is also necessary for the set screw to tightly grip whatever implant element it is urged against so as to lock that element relative to a second element within which the set screw is threaded. Such locking is partially provided by friction. However, positive penetration of the set screw into the element to be set assists in the locking and provides for a more secure lock. A smooth circular surface on the underside of the set screw does not provide digging into or abrasion of the element to be locked and such smooth bottom set screws must rely solely upon the friction generated between a fairly smooth surface and the other element such as a rod for secure locking. In order to overcome this problem, prior art has utilized various structures on the end of the set screw such as points, knurling and cutting rings.

Applicant has found another mechanism for increasing the friction between the set screw and the element to be locked which is to include slots that extend from the sides of the set screw inwardly and open onto the lower face of the set screw. At the intersections of the slots with the bottom face of the set screw are edges which tend to dig or cut into the element to be locked under relatively high torque. Consequently, the set screws incorporating such slots resist greater forces trying to turn a set element relative to the implant in which the set screw is threaded as compared to set screws having solely smooth circular lower surfaces.

SUMMARY OF THE INVENTION

A comparatively strong, but lightweight and low profile set screw that may be used in many applications including in a threaded surrounding bore or between a pair of threaded spaced arms of a first element of an implant to lock or secure a second element of the implant to the first element thereof. The set screw comprises a generally cylindrical body having an outer surface that is threaded, an upper surface and a lower surface. The set screw also includes a structure for driving and torquing the set screw which may include a retained head, a breakaway head, a penetrating bore with polyhedral sides, or upward opening slots or bores within the set screw that each may be utilized in conjunction with a tool for turning and torquing the set screw.

The set screw includes at least one and preferably a pair of side slots. The side slots extend inwardly from the outer threaded surface of the set screw. Furthermore, each side slot intersects with a lower surface of the set screw such that there is a pattern of edges of the slots along the set screw lower surface. Under torque the edges of the slots that are at the lower surface of the set screw preferably dig or cut into and grip the second element to be fixed by the set screw.

In one embodiment of the invention the side slots extend parallel to the axis along the entire length of the set screw.

After the set screw is installed, for example, by use of a break-away head which shears away from the remaining body of the set screw at a preselected torque thereby exposing the side slots or by use of a tool that is received in the slots, the side slots may be accessed by a tool having a similar cross-section to the slots opening upward for purposes of removal.

The side slots may have a variety of cross-sections including rectangular, arcuate or pie-shaped.

In yet another embodiment of the invention, the side slots may be discontinuous in that a lower side slot intersects with the lower surface of the set screw and an upper side slot intersects with the upper surface of the set screw, but the lower and upper slots are discontinuous or non-intersecting with one another. In this manner the lower side slot provides a gripping of the element to be set and the upper side slot allows for removal.

The pitch of the thread is comparatively preferably increased in order to reduce cross threading upon installation. Further, the depth of the thread is preferably decreased to improve the strength of the thread, but is maintained sufficient to prevent slippage between the two threaded surfaces. For a set screw having a 5 to 5.5 mm. diameter a pitch ratio of 0.4 to 0.5 is preferred.

OBJECTS AND ADVANTAGER OF THE INVENTION

Therefore, the objects of the present invention are: to provide a set screw especially for use in conjunction with medical implants and the like wherein the set screw is comparatively strong and yet has a low profile after installation, allows for installation to a preselected torque and is removable from the implant after installation; to provide such a set screw having at least one side slot that extends radially inward from an outer threaded surface thereof and which intersects with a lower surface of the set screw that engages a first element to be set by the set screw such that edges of the slot grip the first element upon torquing of the set screw; to provide such a set screw where there are a pair of opposed side slots; to provide such a set screw having side slots that extend parallel to the axis of the set screw the entire length of the set screw, or alternatively, having separate upper and lower portions with one portion intersecting with the lower surface of the set screw and a second portion intersecting with the upper surface of the set screw such that the portion that intersects with the lower surface aids in gripping and the portion that intersects with the upper surface may be used in installation and/or removal of the set screw by use of a tool; to provide such a set screw which has an outer generally cylindrical surface except where intersected by the side slots and that has a thread with multiple turns of the threads laid thereon in a helical pattern except in the region of said side slots; to provide such a set screw wherein thread depth is comparatively decreased and pitch is increased to produce a finer thread to increase strength of the set screw without increasing size and to reduce the likelihood of cross-threading during installation; to provide such a set screw that may be used equally in conjunction with closed threaded bores or open heads wherein the set screw is utilized as a plug between a pair of inwardly threaded and spaced arms; to provide such a set screw that may be utilized with a breakaway head that breaks from a base of the set screw at a preselected torque, or alternatively, may be used with a retained head that allows torquing to a preselected torque; to provide such a set screw that also alternatively allows installation by use of a tool, either in side slots intersecting with the upper surface of the set screw or with alternative bores in the upper surface of the set screw; and to provide such a set screw which is comparatively easy to manufacture, inexpensive to produce and easily utilized by surgeons during spinal surgery and especially well adapted for the intended uses thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a perspective view of a set screw in accordance with the present invention.

FIG. 2 is a front elevational view of the set screw with the rear elevational view being identical.

FIG. 3 is a cross-sectional view of the set screw, taken along line 3—3 of FIG. 2.

FIG. 5 is a fragmentary and front elevational view of the set screw threadedly installed in a first implant and abutting against a second implant, with the head of the set screw having just broken away from the body due to application of a preselected torque to the head by a tool not shown and with portions of the first implant broken away to illustrate detail thereof.

FIG. 6 is a top plan view of the set screw subsequent to breaking away of the head shown seated in a first implant and abutting against a second implant.

FIG. 10 is a perspective view of a first modified set screw in accordance with the present invention.

FIG. 11 is a front elevational view of the first modified set screw.

FIG. 12 is a cross-sectional view of the first modified set screw, taken along line 12—12 of FIG. 11.

FIG. 13 is a bottom plan view of the first modified set screw.

FIG. 14 is a bottom plan view of a second modified set screw in accordance with the present invention.

FIG. 15 is a perspective view of a third modified set screw in accordance with the present invention that is utilized as a plug.

FIG. 16 is a front elevational view of the third modified set screw.

FIG. 17 is a bottom plan view of the third modified set screw.

FIG. 18 is a fragmentary and front elevational view of the third modified set screw closing an open headed bone screw and engaging a rod located in a channel of the open headed bone screw prior to the breakaway of the breakaway head thereof with portions removed to illustrate detail thereof.

FIG. 19 is a perspective view of a fourth modified embodiment of a set screw in accordance with the present invention.

FIG. 20 is a front elevational view of the fourth modified set screw.

FIG. 21 is a cross-sectional view of the fourth modified set screw, taken along line 21—21 of FIG. 20.

FIG. 22 is a bottom plan view of the fourth modified set screw.

FIG. 23 is a fragmentary and perspective view of the fourth modified set screw shown securing a first element to a second element and a tool for torquing the fourth modified set screw with portions removed to illustrate detail and with the removed portions outlined by phantom lines.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 7:
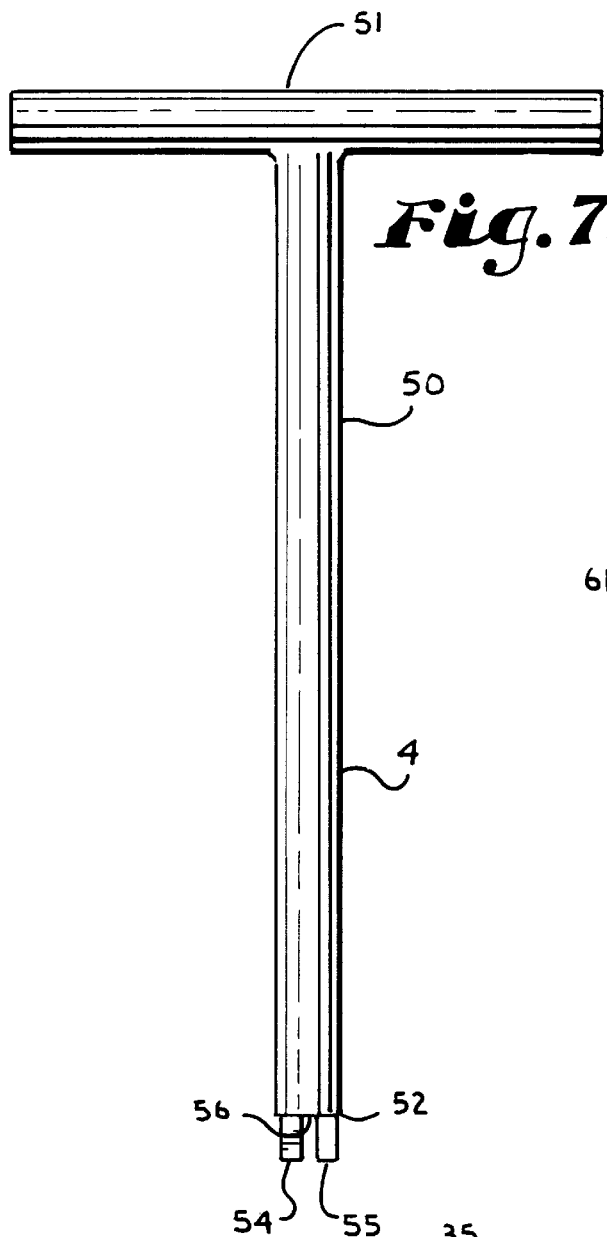
FIG. 7 is a side elevational view of a tool utilized to remove the set screw after installation of the set screw in the first implant, should such removal be necessary.

The reference numeral 1 generally designates a set screw in accordance with the present invention used in conjunction with a medical implant system 3 (FIG. 5) and having an associated removal tool 4 (FIG. 7).

The set screw 1 has an upper section or head 10 and a lower section or base 11 initially joined together along a planar breakaway zone or region 12. The set screw 1 is rotatable about a central axis A that passes longitudinally through the center of the screw 1, and the plane of the breakaway region 12 is generally perpendicular to the axis A.

The head 10 has an outer gripable surface 15, which in the illustrated embodiment includes six planar faces 16 joined together in a hexagonal pattern, such that the faces 16 lie in planes that are parallel to, but are spaced from the axis A.

The surface 15 is sized and shaped to receive a driving or installation tool (not shown) of a conventional type for torquing or clockwise (as viewed from a top 19 of the head 10) rotating the set screw 1. Preferably a driving tool has a hex head for mating with the screw head 10, but any tool that grasps may be functional. A bore 18 extends from the top 19 of the head 10 partially through the head 10 and is coaxial with axis A. The bore 18 preferentially receives a nipple from a driving tool during insertion. Near the top of the bore 18 is an internal chamber or relief 21. A pair of slot tool receivers 22 and 23 extend between the bore 18 and the surface 15 near the head top 19. The receivers 22 and 23 operably receive a portion of a driving tool during installation of the set screw 1. A suitable driving tool for use with the set screw 1 of the present invention is illustrated in my U.S. Pat. No. 5,941,885 on TOOLS FOR USE IN INSTALLING OSTEOSYNTHESIS APPARATUS UTILIZING SET SCREW WITH BREAK-OFF HEAD, which is incorporated herein by reference.

The purpose of the head 10 is to allow a surgeon or other user to use a driving tool to grip the surface 15 and apply rotational force or torque to the screw 1 to firmly set the base 11. The head surface 15 allows good leverage about the axis A and mechanical advantage to allow an installer to gain purchase and apply a locking torque to set the set screw once the set screw 1 is seated. As discussed in greater detail below, the head 10 breaks away from the base 11 at a preselected torque.

Although the illustrated surface 15 is hexagonal in cross section, surfaces of other shapes including non polyhedral shapes may be utilized for the gripable surface 15.

The base 11 has a radially outer surface 24 that is generally cylindrical in overall shape with portions missing, as will be discussed below and that is threaded. The outer surface 24 is coaxial with, but spaced from the axis A. A thread 25 (FIG. 2) winds in a generally helical but discontinuous pattern about the surface 24 with each 360° pass and has associated peaks and valleys.

The thread 25 of the threaded surface 24 is sized and shaped to be received in a threaded implant bore, as described below. The base 11 has a bottom 26 which is generally flat and in a plane perpendicular to the axis A, although it is foreseen that the bottom 26 can be concave, convex or have projections therefrom.

Located between the head 10 and base 11 is the breakaway region 12. The region 12 is in a plane that is typically perpendicular to the axis A. When the head 10 breaks from the base 11, as shown in FIG. 5, a top or upper surface 31 is left on the base 11. The region 12 has a reduced cross sectional area perpendicular to the axis A, as compared to the surrounding regions of the screw 1. It is applicant's theory that this reduced cross-section and geometry thereof is what triggers the breakage at the selected location for the breakaway region 12. Preferably, the breaking of the head 10 from the base 11 leaves the base upper surface 31 relatively smooth and free from burrs, although the metal may deform slightly sideways due to twisting.

The region 12 in the illustrated invention is produced by a combination of two elements. The first element is a pair of slots 35 and 36 (FIG. 3). The second element is an inwardly curved surface 43 located between the head 10 and the base threaded surface 24. The breakaway region 12 is whereat the surface 43 has the least smallest radius and still intersects with the slots 35 and 36.

While the surface 43, and slots 35 and 36 function together to determine the breaking torque and location of break of the illustrated embodiment, it is foreseen that the breakaway torque can be varied and adjusted by changing structural details or geometry of the breakaway region cross-section to increase or decrease desired point of breakage and torque producing breakage. In general the point of breakage is at the smallest cross-section and the smaller the cross-section, the lower the torque at which breakage occurs.

Extending radially inward from the base surface 24 is the pair of slots 35 and 36 which are spaced and non-intersecting. The slots 35 and 36 also extend from and intersect with the breakaway region 12 so as to open onto and intersect with the upper surface 31 after breakage (see FIG. 5) and with the bottom 26. In this embodiment the slots 35 and 36 operably function both as non-planar removal structure located so as to intersect with the base upper surface 31 and are adapted to receive and provide purchase to a tool for removal, such as tool 4, such that the tool 4 may apply torque to the base 11. In this manner the base 11 may be rotated counterclockwise to remove the base 11 that has been previously set from an implant system 3. Each of the slots 35 and 36 is elongate with the greatest length being aligned parallel to the axis A. Each of the slots 35 and 36 is formed by milling, drilling or the like and extends perpendicular to or radially inward toward the axis A, but does not intersect with the axis A. Each slot 35 and 36 is positioned in opposed relationship or diametrically opposite relative to the other.

In this embodiment, each slot 35 and 36 extends entirely along the base outer surface 24. The slots 35 and 36 extend through or intersect with the breakaway region 12 and in the illustrated embodiment extend partly along the surface 43. The depth of each slot 35 and 36 may vary somewhat, but accommodate the removal tool 4 where used for removal. In the illustrated embodiment the slots 35 and 36 each extend approximately 60% of the distance between the lowest part of the threaded surface 24 and the axis A. The width of each of the slots 35 and 36 in the illustrated embodiment is about one third of the diameter of the base 11, but it is foreseen that slots of other size may be used in accordance with the invention, especially considering the size and shape of the tool 4 and the overall diameter of the set screw 1.

As noted above, the slots 35 and 36 also intersect and open onto the base bottom 26. In this manner the slots 35 and 36 form edges 37 and 38 with the base bottom 26. The edges 37 and 38 of the present embodiment are non-coaxial and non-intersecting with the axis A and are non-intersecting with each other. In this embodiment the edges 37 and 38 are laid out with two generally parallel and spaced sides 39 and 40 connected by an inner slightly curved side 41. The edges 37 and 38 tend to dig into or at least frictionally engage a structure against which the screw 1 is set to resist unintended removal and to prevent relative movement between parts of the implant system 3. Thus, in the present embodiment the slots 35 and 36 function both to grip better in setting the screw 1 and to provide for mating with the tool 4 should removal of the set screw 1 be necessary.

Although a pair of slots 35 and 36 is shown in the illustrated embodiment, it is foreseen that three or more slots could be utilized in accordance with the invention and that in some instances even a single slot may be used. Furthermore, it is foreseen that the removal structure of the slots 35 and 36 may be formed of various shaped openings, such as pie shaped or that the removal structure could be simply a flattening of portions of opposite sides of the base 11 near the top surface 31 and extending downwardly to allow a tool to grip the base 11, when the base is screwed into a bore. A wide variety of removal structures may be utilized in the invention. However, the shape and configuration of such structures may be limited when combined with a breakaway head that prevents access to the removal structures until the head is removed. It is also seen that the slots 35 and 36 can be discontinuous between top and bottom or the top and bottom parts of slots can be independent and not aligned.

The upper portions of the illustrated slots 35 and 36 generally differ from conventional screwdriver slots in two ways. In particular, the slots 35 and 36 do not pass through the center axis A of the set screw and the upward projecting sidewalls 48 and 49 on both sides of and positioned between the slots 35 and 36 generally are centrally supported in the present invention whereas such sidewalls produced by a conventional flat screwdriver slot are not centrally supported.

Secondly, the spacing of the slots 35 and 36 toward the radially outer portion of the screw base 11 allows application of force by a tool where the lever arm relative to the axis of rotation A is greatest. In a conventional screw with a standard slot head, a substantial portion of the center of the screwdriver exerts little, if any, force against the screw because the lever arm is so short, most of the force is exerted by the radially outward portion of the screwdriver head. Whereas, in the present embodiment, the tool exerts substantial force along the entire engaging surface.

It is foreseen that in some embodiments the base 11 without the head 10 could be rotated clockwise in an installation direction and torqued into a set position using only a tool such as the tool 4 in the slots 35 and 36 without a head 10 attached to the base 11.

Figure 8:
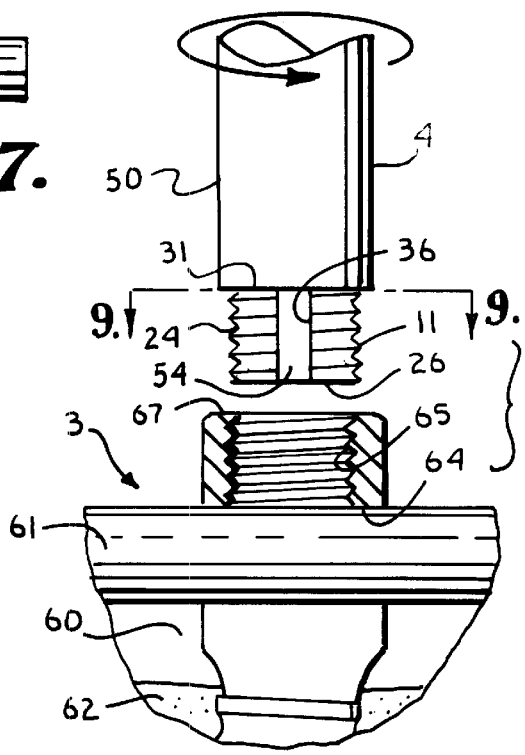
FIG. 8 is a fragmentary and front elevational view of the set screw, first implant, second implant with portions broken away, and tool with the tool having just removed a base of the set screw from the first implant.
Figure 9:
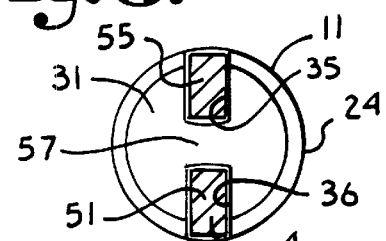
FIG. 9 is a cross-sectional view of the tool and set screw base, taken along line 9—9 of FIG. 8.
Figure 4:
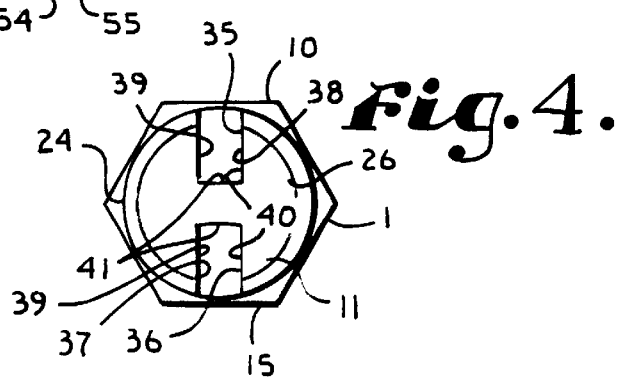
FIG. 4 is a bottom plan view of the set screw.

The illustrated set screw removal tool 4 is T-shaped and includes an elongate shaft 50 with a handle 51 extending perpendicularly in opposite directions from one end thereof. At an end opposite the handle 51 is a set screw engaging tool head 52. As best seen in FIGS. 7 and 9, the tool head 52 includes a pair of axially projecting and slot receiving tabs, lugs or ears 54 and 55. The ears 54 and 55 are separated or spaced by a slot or channel 56. The ears 54 and 55 are sized and shaped to be received inward of the thread 25 within the slots 35 and 36 once the head 10 has been broken from the base 11. The channel 56 spans a center core 57 of the base 11 between the slots 35 and 36. In the present embodiment the ears 54 and 55 are sized and shaped to snugly fill the slots 35 and 36 along the entire length of the slots 35 and 36 except the radially outer portion of the slots 35 and 36 that is located in the region of the thread 25. The ears 54 and 55 may also be utilized in alternative embodiments to insert a base 11 without a head, but this is not always preferred as it is difficult to set the correct torque with only tool 4 and it takes more torque to set the screw 1 than to remove it. The ears 54 and 55 are adapted to be positioned or set in the slots 35 and 36 so as to be received therein, as is illustrated in FIGS. 8 and 9. The channel 56 is sufficiently large in size to receive a center core 57 of the set screw 1 located between the slots 35 and 36. The ears 54 and 55 are also sized to not extend outwardly into the thread 25 of the base 11 or mating thread of the implant system 3. The center core 57 preferably extends to the upper surface 31 of the base 11 and joins opposite sidewalls 48 and 49 of the base 11 together in a comparatively strong construction that does not easily collapse radially inward.

Shown in FIGS. 5, 6 and 8 is the set screw 1 in combination with the medical implant system 3. The medical implant system 3 that is illustrated includes a bone screw 60 and a rod 61. In the illustrated embodiment the bone screw 60 is implanted in a vertebral bone 62. In conventional medical implant systems of the type illustrated herein, there are a wide range of parts that are utilized including hooks, connectors, bars, plates and numerous other elements that are all interconnected together by means of set screws. The set screw 1 of the present invention may be used for interconnecting together any of the various elements, provided that a mating threaded bore or other set screw receiving structure is provided.

In the illustrated embodiment, the bone screw 60 includes a first bore 64 that is sized and shaped to slideably receive the rod 61 that is often positioned so as to be perpendicular to the central elongate axis of the bone screw 60. The rod 61 is positioned in the first bore 64 in the illustration. The bone screw 60 includes a second threaded bore 65 which intersects with the first bore 64 and which is generally aligned to be coaxial with the bone screw 60. The thread of the bore 65 is sized and shaped to receive the thread 25 on the base outer surface 24 of the set screw 1.

The set screw 1 is, thus, first threaded into the threaded bore 65 until the projecting tip 19 engages the rod 61. Thereafter, continued clockwise rotation of the screw 1 transmits an increasing torque to the set screw 1 to set the set screw 1 both within the threaded bore 65 and against the rod 61. As increasing torque is applied to the set screw 1, the torque finally reaches a preselected torque where the head 10 breaks from the base 11 at the breakaway region 12, as is illustrated in FIG. 5.

The torque can be substantially varied according to the system and set screw, but it has been found that a torque on the order of 90 inch pounds is highly effective when setting the set screw 1 so as to prevent relative motion between the various elements of the system 3, including the bone screw 60 and rod 61. The torque with which the head 10 breaks from the base 11 is generally determined by the material of construction of the set screw, the overall diameter of the breakaway region 12, the size and shape of the slots 35 and 36 and the radius of the surface 43, although other factors may be used to set the break point, as noted before, that generally are based on the cross-sectional area of the screw 1 in the selected breakaway region 12.

Subsequent to the head 10 breaking from the base 11, the upper surface 31 of the base 11 is preferably beneath or substantially even with a top 67 of the bone screw 60. In this manner the set screw 1 does not have a projecting head 10 and is comparatively low profile.

Consequently, in operative use, the set screw base 11 secures a first implant, such as the bone screw 60, to a second implant, such as the rod 61, in that the screw 1 is threadably received in the first implant bore 65 and set against the second implant or rod 61 by rotation and application of torque thereto.

Subsequent to the set screw base 11 being set, it is sometimes necessary to remove the base 11. This occurs when the implant system 3 must be adjusted during installation or at a later time when original parts of the system must be removed for some reason. When this occurs, the removal tool 4 is utilized. In particular, the removal tool ears 54 and 55 are placed in the slots 35 and 36. Thereafter, the user applies counterclockwise rotation to the handle 51 to urge the ears 54 and 55 against respective sides of the slots 35 and 36. Sufficient torque is applied in this manner to unseat the base 11. The radially outer edges of the ears 54 and 55 are sufficiently radially inward so as not to interfere with the threads on the interior of the bone screw threaded bore 65. This allows a subsequent set screw 1 to be utilized in the bore 65 to reset the bone screw 60 relative to the rod 61. The tool 4 may also be used to reset or initially set the base by clockwise rotation, if the head 10 is not present in some embodiments so as to allow access to the slots 35 and 36.

While the torque required to unseat the set screw base 11 varies from system to system and with the type of metal used, it has been found that the torque required to unseat the base 11 is often approximately 70% of the torque required to seat the screw 1.

It is foreseen that the set screw 1 of the present invention can be constructed of many different types of materials. When the set screw 1 is to be utilized for medical implants, the material of construction should be as compatible as possible with implantation in human tissue and it has been found that stainless steel and titanium are typically preferred as materials of construction for such uses.

Although the set screw 1 of the present invention is described and illustrated in conjunction with mainly medical implants, as it advantageously provides for many of the requirements peculiar to such implants as opposed to other types of set screws, it is foreseen that the set screw 1 of the present invention may also be used with other types of systems.

The pitch and thread depth of the thread 25 is reduced as much as possible in accordance with the size of the set screw 1, both to produce a finer thread to reduce the likelihood of cross-threading when the screw 1 is inserted in an implant bore, such as bore 65 and to increase the strength of the thread 25 to ensure the thread 25 can be torqued to a preselected torque, without slipping relative to the thread in the threaded bore 65, such as 90 inch pounds. In each embodiment the preferred pitch and pitch ratio varies, but, as an example, a set screw having a 6 mm. diameter has a thread with a preferred pitch of 24 and a pitch ratio of 0.5.

The reference numeral 101 generally designates a second modified set screw in accordance with the present invention. The set screw 101 is quite similar to the set screw 1 and elements that are essentially the same will not be discussed in great detail herein. The set screw 101 includes a head 110, and a base 111 that are joined by a breakaway region 112. The head 110 is of this embodiment is essentially identical to the head 10 of the previous embodiment.

The base 111 is generally cylindrical in shape and has an upper generally planar surface (not shown) when the head 110 is broken away from the base 111 at the breakaway region 112. The base 111 has an outer threaded surface 116 and a pair of slots 119 and 120. The slots 119 and 120 extend the entire length of the base 111 and open onto a base undersurface 122.

The slots 119 and 120 differ in shape from the slots 35 and 36 in that they are pie-shaped, each having a pair of converging walls 125 and 126 that produce a V-shaped surface 127 therebetween. The walls 125 and 126 have lower edges 130 and 131 respectively which operably engage a surface upon which the set screw 1 is set.

The reference numeral 140 is generally directed to a second modified set screw that is illustrated in FIG. 14. The second modified set screw 140 is quite similar to the set screw 101 except with respect to the features that are described below in greater detail.

The second modified set screw has a head 142 that is essentially identical to the head 10 of the first embodiment and a base 143. The base 143 has a generally cylindrical shaped outer surface 145 with a pair of side slots 147 and 148. The side slots 147 and 148 are generally crescent shaped when viewed from the bottom and have an inner wall 50 that is curved or arcuate with a fixed radius. The wall 50 intersects a lower surface of the base 151 at an edge 153. The set screw 140 functions in a manner similar to the set screw 1 described in the first embodiment.

A third modified set screw generally identified by the reference numeral 201 is illustrated in FIGS. 15 through 18. The set screw 201 has some features which are similar to the set screw 1 and those features will not be reiterated in detail, but rather references made to the first embodiment for greater detail regarding common features.

The set screw 201 includes a head 205 and a base 206 connected or joined by a breakaway region 207. The head 205 is generally hexagonal in horizontal cross-section and has a gripable surface 211 that is formed by the juncture of six rectangular faces 13 in a hexagonal pattern suitable for mating with a socket type drive tool. The head 205 includes a shank 214 with a conical shaped outer surface 215 that initially joins with the base 206 at the breakaway region 207. The breakaway region 207 is generally located in a plane whereat the shank 214 has a minimal cross-section and, in the present embodiment, it is located at the intersection of the shank 214 with the base 206.

The base 206 has a generally cylindrical shape except as noted and also has a generally cylindrical shaped threaded radially outer surface 218 that is not continuous. The base also includes a top surface 219 and a bottom surface 220. The base 216 also has a pair of upper side slots 223 and 224 and a pair of lower side slots 225 and 226. A thread 228 wraps helically about the outer surface 218 except in the region of the slots 223, 224, 225 and 226. The thread 228 makes several complete and full passes about the outer surface 218 in the region between the upper slots 223 and 224 and the lower slots 225 and 226. The thread 228 is otherwise discontinuous as the thread 228 makes passes about the surface 218.

The upper slots 223 and 224 are formed by the junction of three walls 231, 232 and 233 that are aligned at generally right angles to one another. In the present embodiment the upper slots 223 and 224 extend approximately ⅓ of the way along the length of the base 206. Furthermore, the breakaway region 206 is positioned between the upper slots 223 and 224.

The lower slots 225 and 226 are also formed by three walls 236, 237 and 238 in a pattern such that the walls 236, 237 and 238 are positioned at right angles to one another. The lower slots 225 and 226 open onto and intersect with the base bottom surface 220 so as to form edges 241, 242 and 243 therewith. The lower slots 225 and 226 also extend approximately ⅓ of the length of the base 205 in the present embodiment.

In FIG. 18 the set screw 201 is illustrated in use in conjunction with a medical implant bone screw 245 and a rod 246. The bone screw 245 includes a threaded shank 251 and a head 252 with a pair of upstanding and generally parallel arms 253 and 254. The arms 253 and 254 form a channel 256 therebetween. Inward and facing surfaces 260 and 261 are threaded with a thread that is mateable with the thread 228 on the set screw base 206.

The rod 246 can be any elongate structure that is adapted to seat in the channel 256. In the present embodiment the rod is simply a circular smooth surface elongate member with a circular cross-section.

In use the base 206 of the set screw 201 is threadably received between the arms 253 and 254 of the bone screw 245 while the rod 246 is in the channel 256. The set screw 201 is then rotated by use of a gripping tool that may be a wrench, a socket or the like until the base bottom surface 120 engages the rod 146, such as is shown in FIG. 18. Subsequently, the set screw 201 is rotated clockwise by application of torque by a tool until the head 205 breaks from the base 206 at the breakaway region 207. Thereafter the upper slots 223 and 224 are accessible by a removal tool should removal be necessary. Furthermore the edges 241, 242 and 243 of the lower slots 225 and 226 engage and assist in gripping the rod 246 to resist either axial movement or rotation of the rod 246 relative to the bone screw 245 or the set screw 201.

While the present embodiment shows the upper slots 223 and 224 aligned axially with lower slots 225 and 226, it is foreseen that such alignment is not necessary in all embodiments.

A third modified set screw in accordance with the present invention is generally identified by the reference numeral 301 and is illustrated in FIGS. 19 through 23. The set screw 301 has certain features which are common to the previous embodiments and those features will not be discussed in great detail. Reference is made to the previous embodiments for greater detail concerning such common features. The set screw 301 has a body 205 that is generally cylindrical in shape with the exception of a pair of side slots 307 and 308 that extend axially the length of the body 305. The body 305 also has a generally planar upper surface 311 and a lower surface 312. Helically wrapped about a radially outward surface 316 of the body 305 is a thread 317 that is discontinuous in the region of the side slots 307 and 308.

The side slots 307 and 308 of the present embodiment have three generally planar walls 321, 322 and 323 which intersect with one another at generally right angles. Each of the walls 321, 322 and 323 intersect with the body lower surface 312 to form edges 326, 327 and 328. The side slots 307 and 308 open not only onto the lower surface 312 but also the upper surface 311.

The side slots 307 and 308 cooperate with a tool such as a tool 332 having a pair of depending and spaced projections that are sized and shaped to fit into the slots 307 and 308 inward of the thread 317 so as to not interfere therewith. The tool 332 may be alternatively used for installing the set screw 301 and also removing the set screw 301, should such be necessary.

In FIG. 23 the set screw 301 is illustrated in use with a first medical implant 335 and a second medical implant 336. The first medical implant 335 is a closed headed bone screw having a head 339 with a bore 340 passing through the head 339. The second medical implant 336 is an elongate rod of generally circular cross-section which is inserted through the head bore 340. The bone screw head 339 includes a second threaded bore 343 that is sized and shaped so as to matingly receive the set screw 301. Preferably the upper surface 311 of the set screw body 305 is at or beneath an upper surface 344 of the medical implant 335.

In use the set screw 301 is typically installed by use of a tool such as tool 332 inserted in the slots 307 and 308 and rotated clockwise while the set screw 301 is positioned in the medical implant bore 343. Rotation is continued until the set screw 301 engages the second medical implant 336. Rotation of the set screw 301 is then continued until the installer is satisfied that a sufficient torque has been achieved to set the set screw 301. The edges 326, 327 and 328 of the slots 307 and 308 frictionally engage and preferably cut or dig into an outer surface 347 of the medical implant 336. The set screw 301 can be removed from the medical implant 335 by reversing the process and rotating the set screw 301 counterclockwise until it clears the threaded bore 343.

It is to be understood that while certain forms of the present invention have been illustrated and described herein, it is not to be limited to the specific forms or arrangement of parts described and shown.

What is claimed and desired to be secured by Letters Patent is as follows:

1. A set screw comprising
   a) A base having an axis of rotation and a radially outward generally cylindrical threaded surface, a top surface and a bottom surface; and
   b) said base having a slot extending radially inward from said threaded surface and intersecting with said bottom surface.

2. The set screw according to claim 1 wherein:
   a) said slot extends between the base top surface and bottom surface.

3. The set screw according to claim 1 wherein:
   a) said slot is a first slot; and including:
   b) a second slot intersecting with said base top surface; said first and second slots not intersecting with one another.

4. The set screw according to claim 1 wherein:
a) said slot is a first slot; and including:
b) a second slot extending radially inward from said threaded surface and intersecting with said bottom surface.

5. The set screw according to claim 4 wherein:
a) said slots are diametrically opposed and said slots each extend between the top surface and bottom surface.

6. The set screw according to claim 1 including:
a) a head secured to said base for rotating and torquing said base.

7. The set screw according to claim 6 wherein:
a) said head is a breakaway head that breaks away from said base at a preselected torque.

8. The set screw according to claim 7 including:
a) a breakaway region between said base and said head.

9. The set screw according to claim 7 wherein:
a) said slot is not accessible when said screw is seated in a threaded bore and said head is secured to said base.

10. The set screw according to claim 1 in combination with first and second medical implants wherein:
a) said first implant threadedly receives said set screw; and
b) said second implant is operably held in locked position relative to said first implant by abutment of said set screw bottom against said second implant.

11. The set screw according to claim 10 wherein:
a) said first implant includes a closed threaded bore to matingly receive said set screw.

12. A set screw according to claim 10 wherein:
a) said first implant includes a pair of spaced arms having threaded facing surfaces and, in use, said set screw is threadedly received between said arm threaded surfaces.

13. The set screw according to claim 1 wherein:
a) said slot has a generally rectangular cross-section.

14. The set screw according to claim 1 wherein:
a) said slot has an arced inner surface.

15. The set screw according to claim 1 wherein:
a) said slot has a V-shaped inner surface.

16. The set screw according to claim 1 wherein:
a) said threaded surface includes a helically wound thread that is discontinuous in the region of said slot and has a fine thread type.

17. The set screw according to claim 15 wherein:
a) said base has a diameter in the range from about 4 to 10 millimeters; and
b) said thread has a pitch in the range from 0.3 to 1.5.

18. The set screw according to claim 16 wherein:
a) said base has a major diameter from 5 to 6 millimeters and said pitch is in the range from 0.4 to 0.55.

19. In a set screw having a generally cylindrical shaped body with a radially outward threaded surfaces and a bottom surface that is generally planar; the improvement comprising:
a) a slot intersecting with both said bottom surface and said threaded surface so as to produce edges along said bottom surface for operably gripping an object to be set by said set screw during usage thereof.

* * * * *